US006560312B2

(12) United States Patent
Cash

(10) Patent No.: US 6,560,312 B2
(45) Date of Patent: *May 6, 2003

(54) MEDICAL USES OF FOCUSED AND IMAGED X-RAYS

(75) Inventor: Webster C. Cash, Boulder, CO (US)

(73) Assignee: Sirius Medicine, LLC, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/055,657

(22) Filed: Jan. 22, 2002

(65) Prior Publication Data

US 2002/0106055 A1 Aug. 8, 2002

Related U.S. Application Data

(63) Continuation of application No. 09/398,468, filed on Sep. 17, 1999, which is a continuation-in-part of application No. PCT/US98/05219, filed on Mar. 17, 1998.
(60) Provisional application No. 60/039,346, filed on Mar. 18, 1997.

(51) Int. Cl.$^7$ .................................................. A61N 5/10
(52) U.S. Cl. ............................... 378/65; 378/64; 378/84
(58) Field of Search ........................... 378/64, 65, 84, 378/145, 147; 600/431

(56) References Cited

U.S. PATENT DOCUMENTS 4,969,175 A * 11/1990 Nelson et al. .............. 378/146
6,359,963 B1 * 3/2002 Cash ............................ 378/65

* cited by examiner

*Primary Examiner*—Drew A. Dunn
*Assistant Examiner*—Jurie Yun
(74) *Attorney, Agent, or Firm*—Dorr, Carson, Sloan & Birney, P.C.

(57) ABSTRACT

The present invention provides methods and instruments for focusing and imaging x-rays using grazing incidence optics and medical and microscopic uses thereof.

11 Claims, 11 Drawing Sheets

MEDICAL USES OF FOCUSED AND IMAGED X-RAYS

RELATED APPLICATIONS

The present application is a continuation of application Ser. No. 09/398,468, filed Sep. 17, 1999, which is continuation-in-part of Patent Cooperation Treaty International Application No. PCT/US98/05219 filed Mar. 17, 1998, which claims the benefit of U.S. Provisional Patent Application 60/039,346, filed Mar. 18, 1997.

BACKGROUND OF THE INVENTION

1. Field of the Invention

The present invention provides methods and instruments for focusing and imaging x-rays using grazing incidence optics and medical uses thereof.

2. Background of the Invention

X-ray radiation is used for many medical applications. For example, radiation is used to kill tumor cells that are difficult or impossible to treat with surgery. This "radio-surgery" usually employs what are typically classified as gamma rays—photons with energy in excess of 1 MeV.

Gamma rays are used (instead of x-rays with E<100 keV) because to kill diseased cells requires a dose of radiation comparable to the dosage needed to kill healthy cells. Thus, total dose to a tumor must exceed the dose to surrounding tissue ("therapeutic ratio") if the therapy is to be effective, i.e., kill the tumor cells but not damage healthy tissue. Currently, a proper ratio is achieved by directing the beam at the tumor from multiple directions by scanning the beam or pointing multiple beams at the tumor. By this method, the point where the beams cross receives a higher dosage than the healthy tissue the beams must pass through on the way. One problem with this method is that the beam intensity drops rapidly as it passes through the healthy tissue because of Compton scattering by electrons in the tissue. By the time an orthovoltage x-ray beam reaches the center of the brain, for example, it has been reduced to about 20% the intensity it had at the skin surface. Thus, it would require irradiation from five independent directions just to bring the flux at the center of the brain back up to the (presumably non-lethal) level of the skin. Because irradiation from so many directions is required to achieve a good ratio of tumor to skin exposure, the technique is problematical.

However, because of relativistic effects, Compton scattering drops by a factor of about two as the energy of the beam rises to the mega-volt range. With gamma rays, almost half the beam intensity survives to the center of the body. This allows improved exposure ratios between healthy and diseased tissues to be achieved with reasonable geometries. Additionally, the buildup effects of the relativistic Compton electrons keep skin dosage even lower, a highly desirable cosmetic result. However, problems caused by gamma rays include side scatter, over shoot, and low intensity beams. Precision below a target size of about 5mm is not possible. By using a beam in the 50 keV range, the beam is cleaner, sharper and overshoots the target area less.

There is a rising incidence of breast cancer in the US, making it the leading cause of death for women in the 40 to 50 age group. One out of nine women will develop breast cancer in her lifetime. Mammography is being promoted as a major line of defense against breast cancer. Through early detection, women may have a better chance of receiving effective treatment. However, there are problems with mammography, and significant improvements are needed.

The problems arise from the goal of imaging the soft tissue of the breast. A tumor is not significantly different in composition or density from the fibrous and glandular tissues of the breast, although it is of higher density than the adipose tissue whose content increases with age. For this reason, mammography is of limited value in young women where the incidence of cancer is lower, and the ability to detect a tumor is lower. The tumor usually becomes visible by eventually displacing the lower density adipose tissue. By this time, unfortunately, the tumor has become of substantial size. Improved contrast for seeing small tumors and improved ability to recognize unhealthy tissue at an early stage of development are central goals.

In order to enhance the contrast of the x-ray image, mammograms must use very low energy x-rays, typically 18 keV. The fractional energy absorbed by a small feature (e.g., a tumor) rises as the energy drops, creating higher contrast. Additionally, as the energy of the photons drops, the percentage absorbed in accordance with the photoelectric effect rises, reducing the scattered radiation component on the film or other recording medium, and thus enhancing contrast. Grids are usually employed as well to further reduce the scattered component. The problem with shifting to low energy photons is a rapid increase in the overall absorption of radiation in the breast. In a typical mammogram, less than 1% of the incident radiation emerges. As a result, the intensity of the radiation source must be increased by a factor of 100, subjecting women to much higher dosage in mammograms than is encountered with most diagnostic x-rays.

X-ray optics also can be used for microscopy. Indeed, the first grazing incidence optics (developed in the late 1940's and early 1950's) were applied to microscopy. There is a variety of reasons why x-ray microscopy is of interest, but the field has been stalled for lack of a practical imaging system.

The first rationale for x-ray microscopy is simply resolution. As Fraunhoffer proved early in the 19th Century, the resolution of a microscope is fundamentally limited at about one wavelength of radiation. Thus, light microscopes (those that use visible radiation) are limited to about $0.5\mu$ resolution. A shift to the ultraviolet can extend resolution to about $0.2\mu$. The very short wavelengths of x-rays can potentially break through this barrier.

A second relevant property of x-rays is their ability to penetrate matter. Thus, unlike electron microscopes, an x-ray microscope can be used on live cells in an air environment. In addition, x-ray absorption is dependent on material density and elemental composition. Thus, changes in absorption across K edges can lead to contrast enhancement, creating an exquisite sensitivity to elemental composition not found with light or electrons.

The design of an x-ray microscope, using grazing incidence optics, is analogous to the design of a conventional light microscope. A light source is placed below a slide containing a sample. The radiation penetrates the sample, and is partially absorbed. The light diverging from the sample is re-imaged and magnified by an optic. A detector is placed at the focal plane to record the image.

The present invention solves the problems discussed above, and others related to medical and microscopic uses of x-rays, by providing methods and instruments for medical uses of focused and imaged x-rays.

SUMMARY OF THE INVENTION

The present invention relates to medical and microscopic (together "biological") uses of focused x-rays. More specifically, the invention relates to use of focused x-rays for radio-surgery, mammography and microscopy. The x-rays may be focused using grazing incidence optics or other x-ray optical methods. A preferred method employs spherical mirrors for such grazing incidence optics. Even more specifically, the optical system disclosed in U.S. Pat. No. 5,604,782 may be employed. Also provided are apparatuses for use in the methods. In particular is provided a radio-surgery, a mammography and a microscopic instrument employing grazing incidence optics.

DETAILED DESCRIPTION OF THE INVENTION

Figure 1:
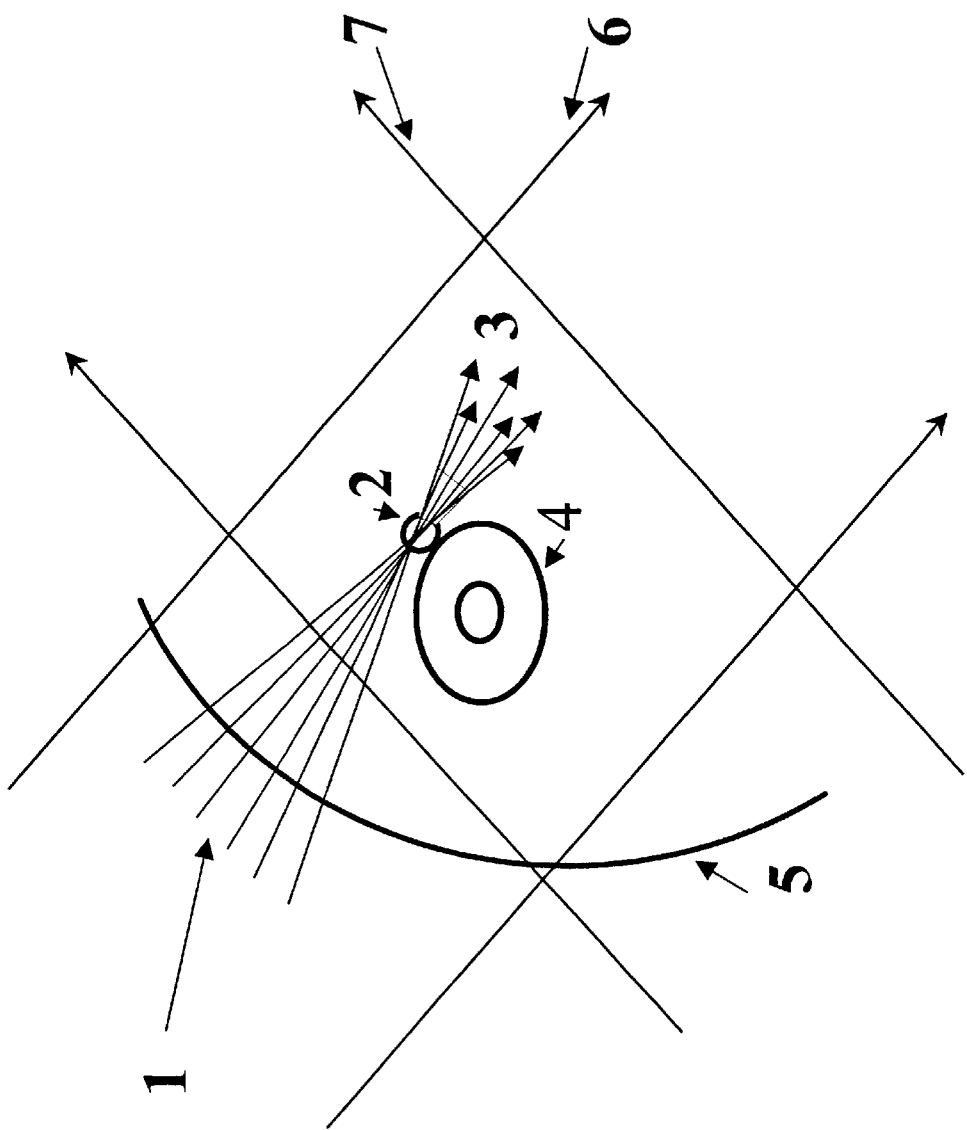
FIG. 1 shows a converging beam of orthovoltage x-rays focused on a tumor that is situated near the spine.

The present invention provides apparatuses and methods for biological uses of x-ray optics. In particular, the invention relates to uses of focused x-rays for medical uses and x-ray microscopy. More particularly, the medical uses include x-ray radiation therapy, radio-surgery and x-ray diagnostics. The preferred x-ray optic system is described below.

As used herein, "focused" and related terms, e.g., focusing, as applied to x-rays, includes line and point focusing, imaging and collimating, unless otherwise stated.

The x-ray optical systems employed herein are based on the use of grazing incidence optics. It is a generally known phenomenon that x-rays, if incident upon a sufficiently polished surface at a sufficiently low angle, are reflected rather than absorbed or transmitted. The critical angle below which the radiation reflects is a function of the energy of the x-ray and the electron density in the reflecting surface, e.g., a metallic surface. Use of coherent reflection in multilayer coatings can increase the critical angle by up to a factor of ten. Multilayer mirrors are made by depositing alternating thin layers of two elements with different indices of refraction. This creates constructive interference and, therefore, high reflectivity at one wavelength.

Because of the low grazing angles, long geometries are naturally encountered, and nested mirrors may be used to increase the collecting area or solid angle of the optic. Two well known types of grazing incidence optics are useful in the present invention. "Wolter optics," as used herein, comprises nested paraboloids or cones (H. Wolter, "Spiegelsysteme Streifender Einfalls als Abbildende Optiken fur Roentgenstrahlen," Ann. Phys., 10, 94–114 (1952) and specifically incorporated herein by reference). Second, "Kirkpatrick-Baez optics," as used herein, comprise quasi-flat mirrors and are used to focus in one dimension, with two reflections required for a two-dimensional focus (P. Kirkpatrick and A. v. Baez, "Formation of Optical Images by X-rays," J. Opt. Soc. Am., 38, 766–774 (1948) and specifically incorporated herein by reference). Both classes are applicable to the invention.

The present inventor has developed an x-ray optic (U.S. Pat. No. 5,604,782 and specifically incorporated herein by reference), primarily based on spherical lenses, that uses grazing incidence optics to refocus radiation diverging from a source. This x-ray optics system also can be used in some applications of the instant invention and is referred to herein as "spherical optics."

An equivalently shaped x-ray beam can be created by moving a pinhole-collimated pencil beam while keeping the beam pointed at one place in space. While this is practical, it leads to severely low fluxes, and impracticably long treatment times.

Using grazing incidence, an array of mirrors acts like a lens, referred to herein as "grazing incidence focusing optics." X-rays diverging from a source can be refocused to a spot or made into a parallel beam. Our invention concerns the generation and use of such beams for radio-surgery and diagnostics. The characteristics of the converging beams determines their uses.

Orthovoltage Radio-Surgery

We have evaluated the effects of a concentrated x-ray beam for use in radio-surgery. Photon energies above one MeV have been used for radiotherapy and radio-surgery because the buildup effect minimizes dosage to the skin at the entrance point. For radio-surgery (as opposed to radiotherapy), a properly configured beam of orthovoltage x-rays will provide much higher flux at the target than at the skin. This means that orthovoltage x-rays can be safely used for surgery.

Assume there is an orthovoltage x-ray source at a distance D from the skin of the patient. Further, assume that the optical path length of the orthovoltage beam is given by $\tau$ (typically 5 cm in tissue). Then, the intensity of the radiation at a depth x in the tissue will be given by $$I = \frac{I_0 e^{-\frac{x}{\tau}}}{(D+x)^2}$$

where $I_0$ is an arbitrary intensity parameter. This leads to monotonically decreasing beam intensity, one which has less than 30% the dose at 50 mm than it has at the skin.

However, with a converging beam that comes to a focal spot of diameter s at a depth d in the tissue, the beam intensity will be given by:

$$I = \frac{I_0 e^{-\frac{x}{\tau}}}{s^2 + \frac{(d-x)^2}{f^2}}$$

where x is the depth in tissue, and f is the focal ratio of the beam. Note that when $$\left(1 + \frac{d^2}{s^2 f^2}\right) e^{-\frac{d}{\tau}} \geq 0$$

the intensity of the beam at the focus (x=d) is greater than the intensity of the beam at the skin (x=0). For example, if the spot (s) is 3.2 mm, the focus is at a depth (d) of 75 mm, and the beam is f/7, the flux at the focus will be 2.7 times that at the skin. This ratio is large enough to kill diseased tissue at the focus point without damaging the healthy skin tissue. Scanning the beam in a manner analogous to that already in use with mega-volt radio-surgery is also possible to further enhance the ratio by effectively further decreasing the value of f. It is a constraint on the effective value of f in the design that makes this desirable property possible. Value for effective f should be well below 50 if high ratios below the skin are to be achieved. Values below 20 are desirable.

Another property of the focused x-ray beam is the rapid falloff on the far side of the focal point. Post-focus, the divergence of the beam and the exponential decay of the beam due to absorption combine to cause a very rapid drop in local dosage. For the f/7 beam, the intensity falls to below 50% of peak dosage in about one centimeter. This means that tumors residing close to sensitive areas, like the optic nerve, can be treated without damaging the nearby sensitive structures. Currently, therapy which uses mega-voltage x-ray beams means that overshoot of the beam makes such close exposure dangerous.

Dose deposition differs when using orthovoltage x-rays for radio-surgery. With radiation at 1MeV and above, the only interaction of the photons off electrons in the tissue is Compton scattering. Most of the energy of the photon is transferred to the electron, creating a relativistic electron that can travel centimeters through the body, leaving a wake of broken molecular bonds behind. This means that it is very difficult to create small regions of intense local ionization. Orthovoltage photons also interact primarily (though not exclusively) through Compton interactions. However, 58 keV photons transfer only about 10% of their energy to the scattered electron. The other 90% remains in the scattered photon, which continues in a random direction. The scattered photon eventually leaves the body or undergoes another interaction. Since the average distance traveled is about 50 mm, half these photons interact within a 100 mm diameter. Thus, there can be more integrated dose in a 100 mm diameter than there is within the direct beam. However, as long as the target is significantly less than 1000 cc in volume (which nearly all radiation targets are) the dose that the nearby healthy tissue experiences is also significantly below that in the target. Therefore, the integrated dose is not a problem.

The post-focus falloff of the beam is dramatic and useful in the treatment of tumors near critical structures. However, the lateral falloff is even more pronounced. FIG. 1 shows an x-ray beam 1 focused on a tumor 2 lying next to the spinal cord 4. The beam enters the surface of the body 5, reaches its focus at the tumor 2, and then falls in intensity rapidly post-focus 3. The beam is positioned such that the critical structure (e.g., the spinal cord) lies outside the beam to the side. The low energy of the Compton scattered electrons from interaction with the primary beam allows them to travel at most a few hundred microns laterally from the site of the interaction. Therefore, they cannot reach the spinal cord or other nearby critical structure. The Compton-scattered photons from the original beam travel on the order 50 mm before being absorbed. Thus, the dose experienced by the tissue about 500 microns or more lateral to the beam edge will be less than 2% that seen in the beam. This allows very delicate surgery to be performed near critical structures.

The focused beam may also be aligned with the help of diagnostic beams that allow one to place a target in "crosshairs" in real time. FIG. 1 shows beams (6 and 7) that can be used to allow real-time positioning of the focus. Such a capability allows treatment of small tumors in otherwise dangerous areas, such as next to the spinal cord. Similarly, small tumors in soft tissue, where tumor position can shift between diagnosis and therapy, are treatable.

Another advantage of the focused beam is its speed. By redirecting a large flux of diverging x-ray radiation to a spot, the local flux is significantly enhanced. Better use of the photons generated is made as more reach the target and fewer hit aperture stops.

Figure 2:
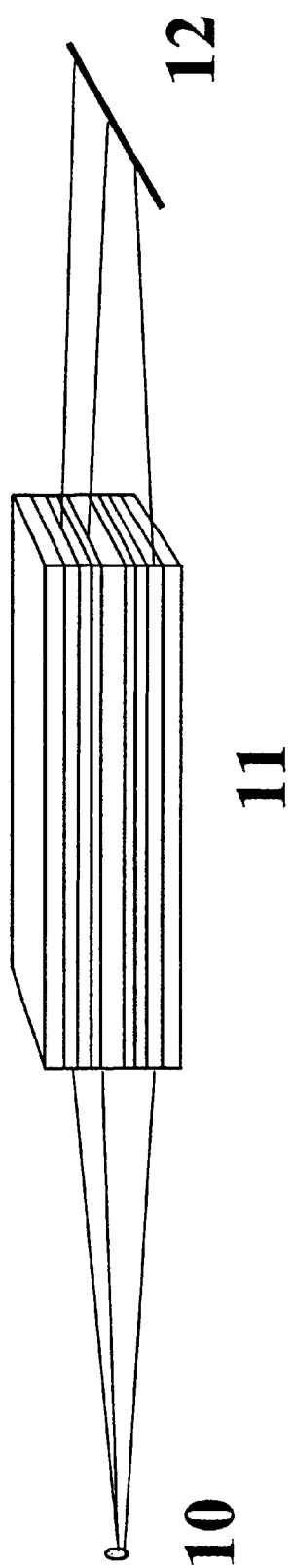
FIG. 2 is a schematic that shows flat, or nearly flat, plates in a stack concentrating x-rays to a line focus.
Figure 3:
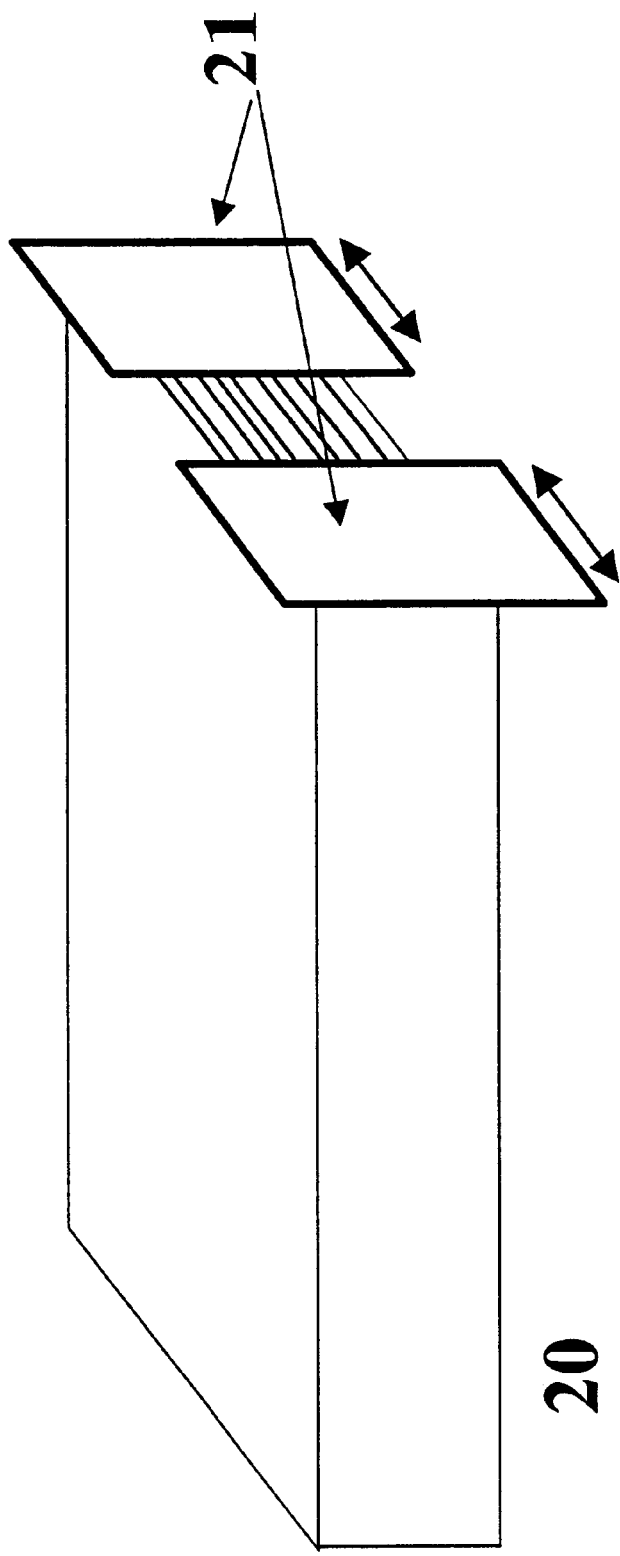
FIG. 3 shows a stack of plates creating a line focus together with plates on the exit aperture that control the length of the focal line.

The design of the grazing incidence lens that converts the diverging beam to converging encompasses a variety of embodiments:

Kirkpatrick-Baez One Dimensional: These consist of one or more mirrored plates arranged to take diverging light and bring it to a line focus in one dimension. The plates can be flat, or nearly flat. A curvature in the surface of the plate allows a finer focus. Multilayers on the plate surfaces allow higher reflection angles to be achieved. This allows the mirror array to be shorter and the range of divergence angles to be greater, leading to faster mirror arrays. A schematic of such an array is given in FIG. 2. In this case, the rays diverge from the point source 10, are reflected off the flat mirrors in the array 11, and are focused to a line 12. The output of such an array 20, in FIG. 3, can have aperture stops 21 placed on it to set the length of the focus line.

A mirror array wherein each x-ray undergoes multiple reflections in the same direction sequentially can bend the beam through larger angles yielding a faster beam. The present inventor has developed an x-ray optic (U.S. Pat. No. 5,604,782) that allows extremely fine focusing using sequential spheres to correct for coma. This line focus can be used to sweep across large targets with high uniformity of dose.

Figure 4:
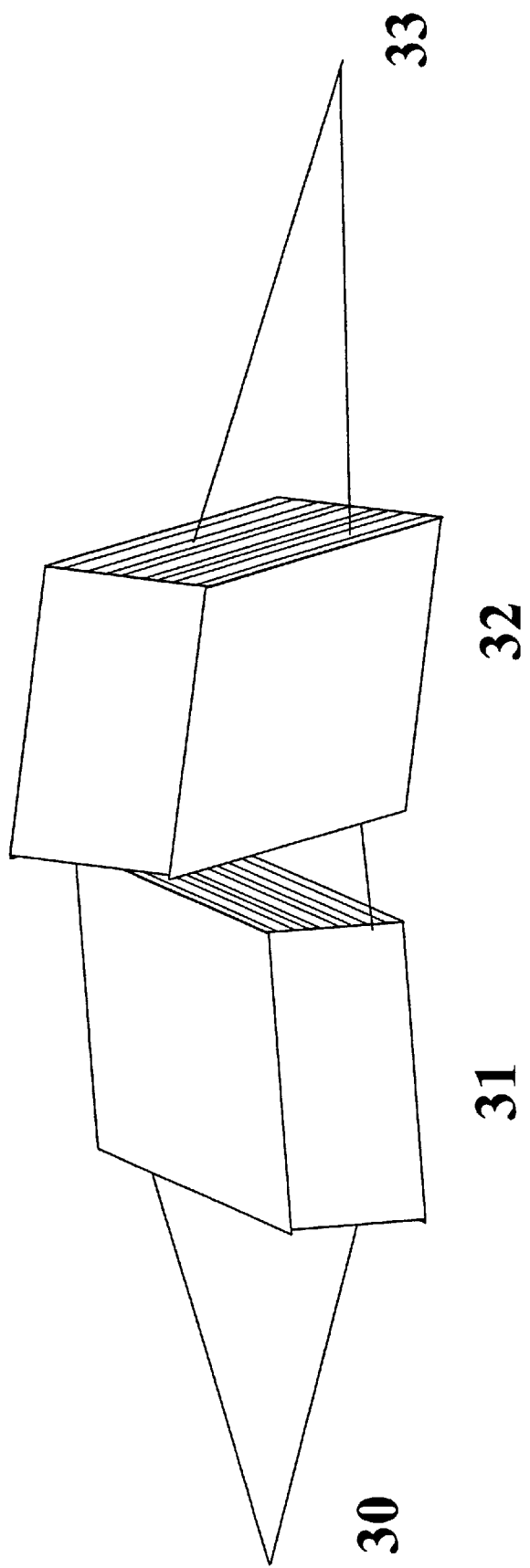
FIG. 4 shows x-rays diverging from a point, being concentrated by two reflectors in turn, and returning to a two dimensional focus.

Kirkpatrick-Baez Two-Dimensional: To create a two-dimensional focus using the Kirkpatrick-Baez approach (supra), two arrays of mirrors are set to reflect the x-rays sequentially. FIG. 4 shows that rays diverging from a point source 30 pass through a one line focus array 31, then through another 32 set orthogonally to focus in the second dimension. This creates a point focus at 33.

Figure 5:
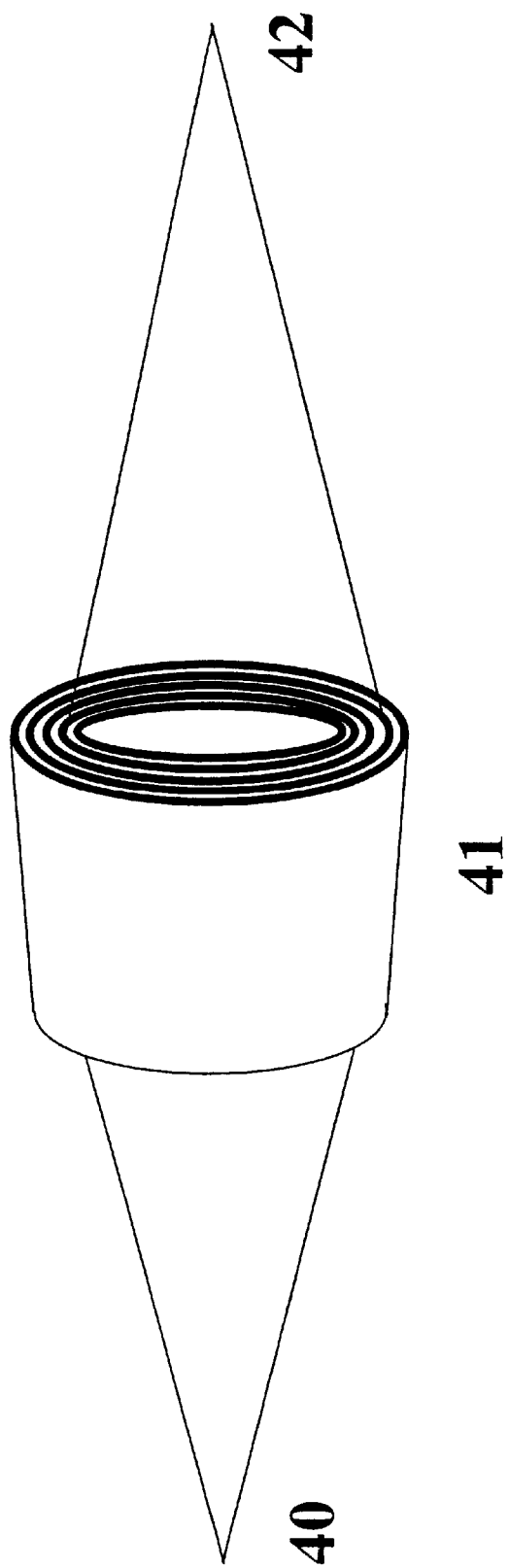
FIG. 5 shows concentric shells focusing x-rays in two dimensions at once.

Wolter Geometry: Two-dimensional focusing can be done using optics with cylindrical symmetry as well. These are generically known as Wolter optics (supra). The simplest optic is a cylinder. The x-rays reflect off the inside of the cylinder toward a common focus. Toroids and ellipsoids can be used instead of cylinders to improve the quality of the focus. Thin shells may be nested to increase the angular grasp of the optic as in FIG. 5. Rays from a point source 40 reflect on the inside of the shells 41 to come to a point-like focus at 42. Similarly, multiple cylinders in sequence can be used to produce a sequence of reflections to improve the overall grasp and speed of the optic.

Focused beams can be applied to a variety of surgical procedures that require the killing, partial killing, or removal of a structure in the body. The procedures that can be done with focused orthovoltage x-ray beams include: a) killing tumors, particularly those that are small and difficult to reach surgically, b) arteriovenous malformation corrections, c) pallidotomy, d) nerve ablation, and e) repair of macular degeneration.

Figure 6:
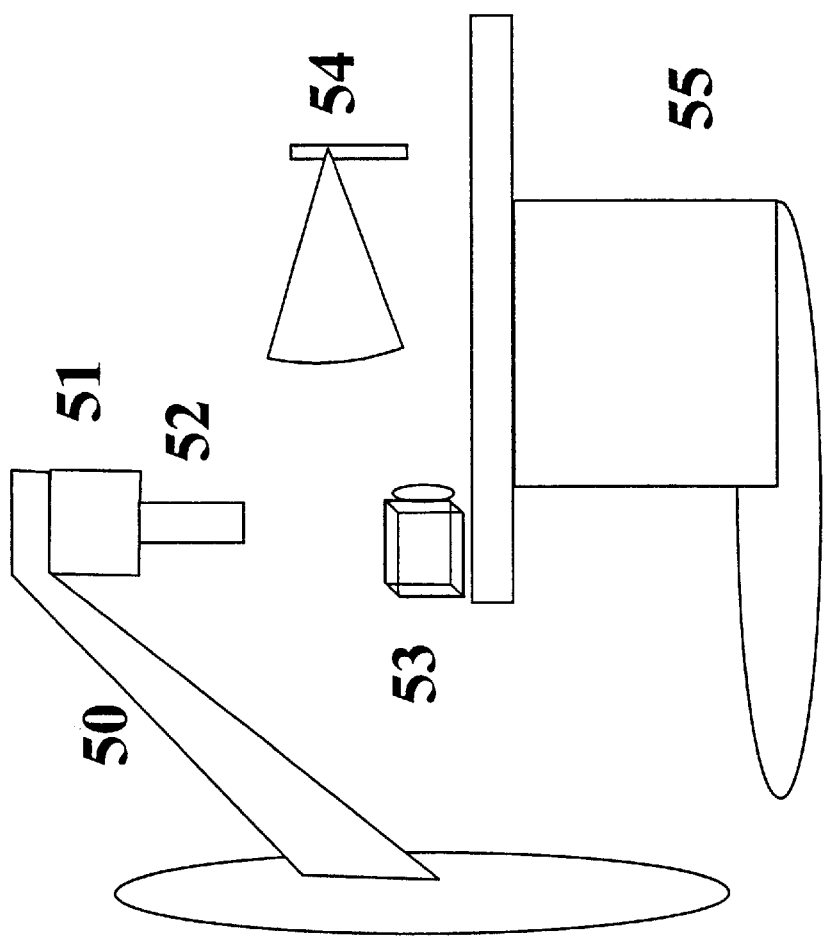
FIG. 6 shows an apparatus for stereo-tactical radio-surgery using orthovoltage x-rays.

The component parts of a typical orthovoltage surgery device using focused x-rays are illustrated in FIG. 6. Radiation source 51 generates an x-ray beam with adequate flux, for example, about 1200 cGy to a 3 cm tumor, in a reasonable time, e.g., under one hour, to support therapy. Grazing incidence focusing optics 52 shape the beam to conform to the size and shape of the target. A source gantry 50 on a rotational arm aims the radiation source at the therapeutic target and may be used to move the x-ray beam through a prescribed arc as treatment proceeds. Treatment table 55 accurately places and stabilizes the patient's position throughout the procedure. A control console may be used to operate the radiation source, position the patient and direct the beam. A stereo-tactic frame 53 may be affixed to the patient to create external reference points for the target. The tumor is identified with a CT and MRI imaging systems, and positioning angles are determined with the treatment planning PC. A visible laser 54 is used to align the x-ray beam to the target using the stereo-tactic frame. A treatment planning PC ("TPPC") is used to plan the angles and sweeping arcs that maximize radiation doses to the target site to ensure minimal damage to surrounding organs and tissue. The TPPC creates a three dimensional model of the patient and the target based on the output of CT and MRI scans. The TPCC is then used to create an optimal set of scans with the x-ray beam to maximize dose to the target and minimize dose to healthy tissue. Software that can be used as the basis for such a PC system can be obtained from Leibinger (Dallas, Tex.).

Figure 6A:
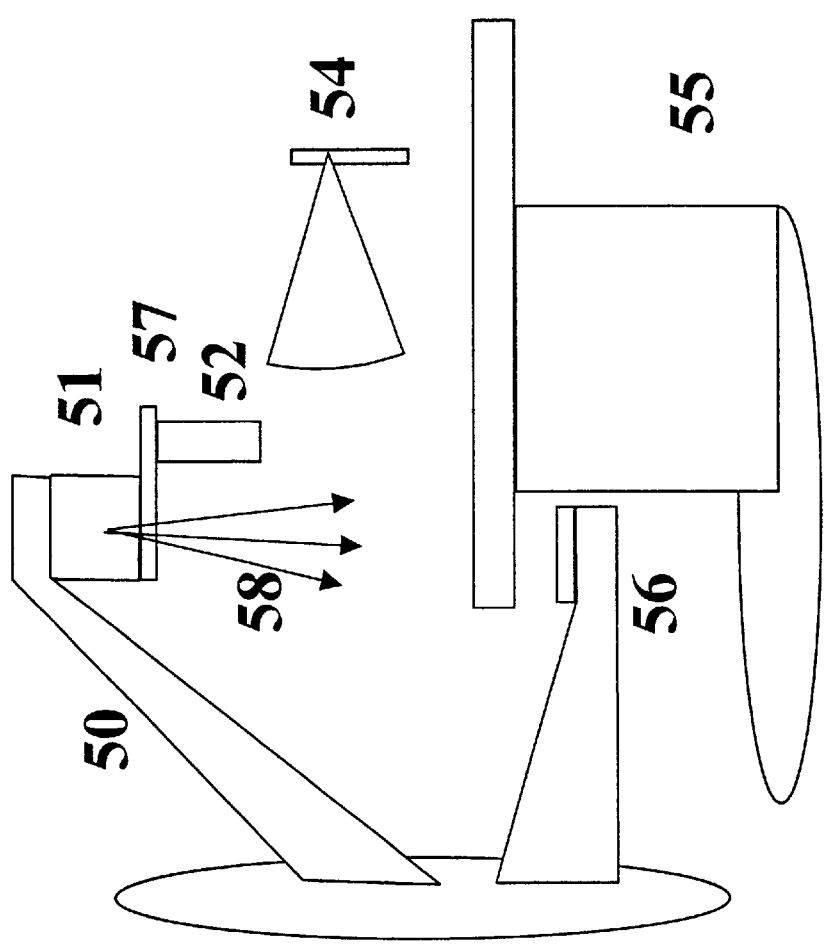
FIG. 6a shows the apparatus of FIG. 6 with a digital detector 56 on a second swing arm below the patient.

A highly attractive alternative to using the stero-tactic frame 53 to create a reference to an external coordinate system is to create the diagnostic information in situ. In FIG. 6a, we show the orthovoltage surgery device without the stero-tactical frame. Instead, as many simulator systems have, there is a digital detector 56 on a second swing arm below the patient, that rotates about the same axis as the source and thus stays opposite. The x-ray optic 52 can be removed quickly from the beam using a translation stage 57, allowing the x-ray beam to pass through the patient directly. As the axis is rotated, this constitutes a CT simulator. The information can be inverted to create 3-D images in the CT mode. The images are available to the doctor immediately. The target in the patient can then be defined in the coordinate system of the optic. Reinsertion of the optic and irradiation of the target can proceed within seconds. The patient does not need to move. This constitutes a major improvement in method over existing procedures which involve transferring and re-establishing coordinates.

If the beam is to function with the desirable lateral property discussed, then the beam must be designed with an additional constraints in mind. The beam will re-image the source of x-rays, and that source must be is small compared to the fall-off distance required. That is, a 1 mm spot of x-rays within the source will lead to a 1 mm fall-off distance in the lateral response. This is excellent by today's standards. An x-ray source with a large, 1 cm spot will exhibit a 1 cm fall off distance. Thus, for extremely tight targets, where a lateral falloff of substantially below 1 mm is required, it may be necessary to use a microfocus source.

In summary, a converging x-ray beam can be used to deliver a fine, concentrated beam. The focused beam improves skin to tumor dosage ratios. Fast fall-off, post-focus and lateral to the beam, allows treatment near sensitive areas. Fine targeting control allows treatment of tumors close to sensitive places, and in areas where the targets could shift. Concentration of the flux reduces treatment time.

Diagnostic Imaging and Mammography

It is known that moving the x-ray detector plane back from the patient when doing x-ray imaging can provide an improved signal-to-noise ratio by allowing scattered radiation to miss the detector. However, the diverging radiation makes the image larger as the detector is moved away. At the same time, the blur caused by the size of the x-ray emissive spot in the x-ray source tube blurs the resolution of the image. For this reason, there is interest in source tubes with very small x-ray spots. Smaller tubes can solve the resolution and scatter problem, but require a very large detector.

Figure 7:
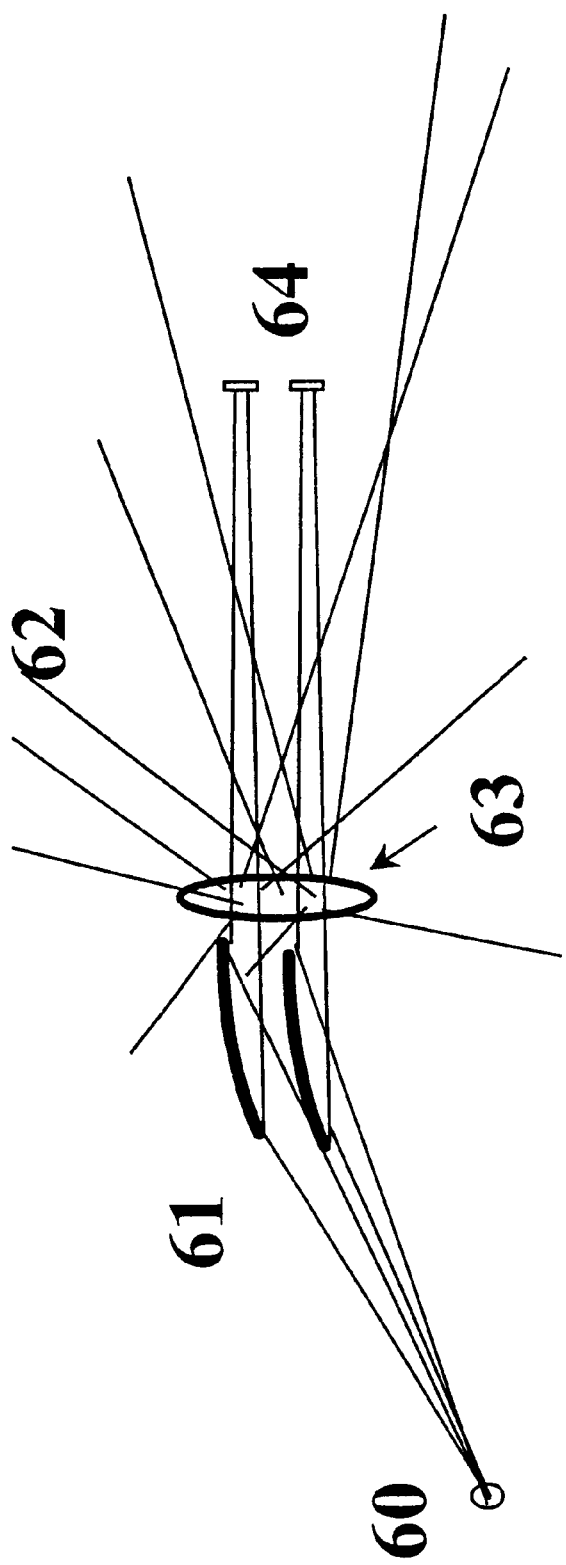
FIG. 7 shows an apparatus for improved mammography using focused x-ray beams. Diverging x-rays are refocused and filtered prior to reaching the patient. Scattered radiation misses the detectors because they can be small and at a large distance from the patient.

The present invention provides a mammography unit as set forth in FIG. 7. An x-ray beam diverges from a point source 60. Grazing incidence x-ray optics 61 as described above, render the beam parallel and filter unwanted photon energies prior to the beam striking the patient represented schematically 63. Scattered radiation 62 does not strike the detectors 64. The nearly total removal of scatter from the image produced on the detectors creates higher contrast, and allows the Bucky grid of conventional mammography units to be removed. Therefore, patient dose can be decreased by about a factor of three. If the beam is made to slightly converge, then the image size is reduced before it reaches the detector, allowing it to be matched to the detector size, a substantial advantage when using electronic detectors. Thus, the use of grazing incidence x-ray focusing optics can create a higher contrast image (no scatter is detected) on a less expensive and more compact detector.

However, even more compelling reasons for using grazing incidence optics emerge using higher photon energy. For example, at 34 keV, x-ray absorption by the breast is significantly lower, as summarized in Table 1. Twenty-seven times more radiation emerges from the breast in the primary beam than with conventional energies used for mammography. Since the beam can be made highly monochromatic by optical coatings, e.g., multilayers, the low energy tail of emissions from the source is removed before entering the patient, reducing the dose by a factor of two. Finally, because there is no grid, the total dose reduction is over 100 times.

TABLE 1*

| Lower Absorption | X27 |
| --- | --- |
| Remove Grid | X3 |
| Spectral Shape | X2 |
| Total Dose Reduction | X162 |
| Peak Dosage | X5 |
| Peak Dose Reduction | X810 |

*By shifting from 18 keV to 34 keV (iodine edge), the dose required to achieve constant signal drops by a factor of over 100. Since the dosage is highest at the entrance side, the peak dosage drops even more.

In current mammograms, over half the radiation is absorbed in the first one fifth of the breast. With the lower absorption at higher energies of between about 25- and 34 keV, the x-ray dose is more uniformly administered, reducing peak dosage. With all effects included, the peak dosage drops by nearly a factor of one thousand.

However, lowering the dose has a cost. As one moves from 18 to 34 keV, the fraction of the radiation absorbed or scattered by a small feature decreases by about a factor of three, reducing the contrast by the same factor of three. Thus, features would have to be much larger to be visible, and that would be unacceptable. The contrast loss is partially offset by the complete elimination of scattered radiation at the detector, as shown in Table 2. However, there is still room for improvement.

TABLE 2*

| Absorption | X0.3 |
|---|---|
| Remove all scatter | X1.5 |
| Total Contrast | X0.45 |
| Signal x9 | X3 |
| Total Contrast | X1.35 |
| .03% iodine | X2 |
| Total Contrast | X2.7 |

*Contrast is reduced a factor of three at 34 keV. However, this is partially offset by scatter reduction. By increasing signal, contrast can be increased while dose is still well below current levels. An iodine-bearing compound can further enhance detection.

The shortfall in contrast can be alleviated by increasing the signal in the detector. The effective contrast in a linear detector scales as the square root of the signal. Therefore, by increasing the signal detected, the effective contrast can be greater than before. Thus, a typical arrangement as provided by the current invention would allow for a mammogram with ten times lower dosage than before, coupled with twice the contrast.

While excellent contrast is a requirement in effective mammography, there already is a problem in interpreting what information is produced by mammography. The complexity of breast tissue leads to the appearance of many features on the mammogram, most of which are from healthy structures. Correctly identifying which features are potentially dangerous can be difficult. As CT scans of the body have shown, three-dimensional imaging brings subtle features out more clearly. By shifting the x-ray energy to about 34 keV, the breast will need not be compressed, and images from several directions can be taken to create a 3-D image.

Finally, interaction of focused x-ray beam and the tumor must be considered. If a pharmaceutical comprising a heavy element that is transported preferentially to a tumor is introduced, then contrast can be improved dramatically, allowing detection and identification at an earlier stage of tumor development. Such elements are well known, including, for example iodine and gadolinium. If that heavy element is iodine, then a mammography setup can be arranged that includes two images taken as described above. For example, the first would use radiation at 35 keV, above the iodine edge. The second would be recorded using 32 keV radiation, below the edge. Comparison of the two images would then show a detailed distribution of iodine in detail.

In summary, using optically-focused x-rays, mammography can be performed with reduced dosage. Contrast can be increased at the same time dose is reduced. Finally, heavy element compounds can further enhance contrast. Converging beams produced by grazing incidence optics allow the image to be recorded on a small detector with conveniently-sized pixels.

Microscopy

Figure 8:
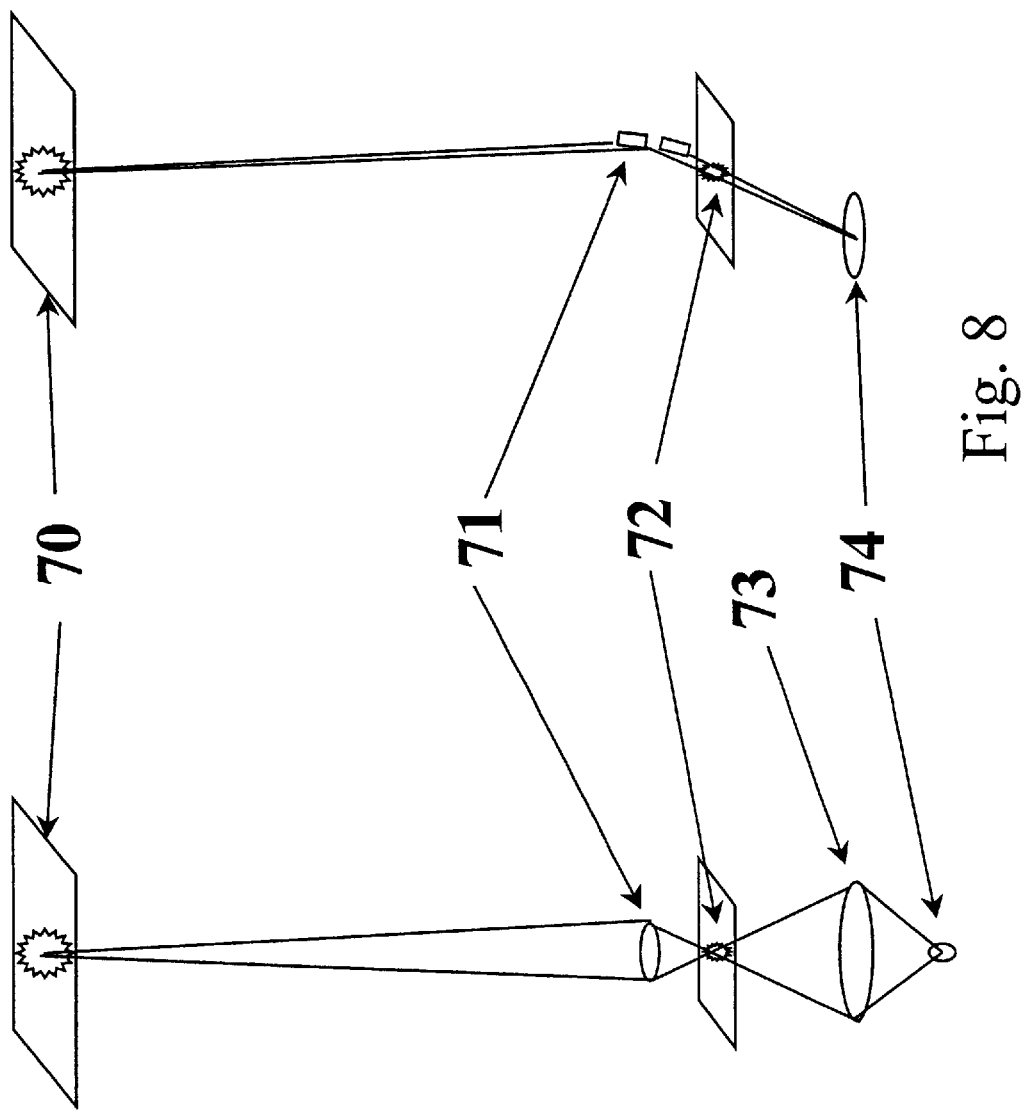
FIG. 8 shows an x-ray microscope (right) compared to a conventional light microscope (left). The devices are conceptually similar if one uses a four (or more) spherical mirror lens in the x-ray microscope.
Figure 9:
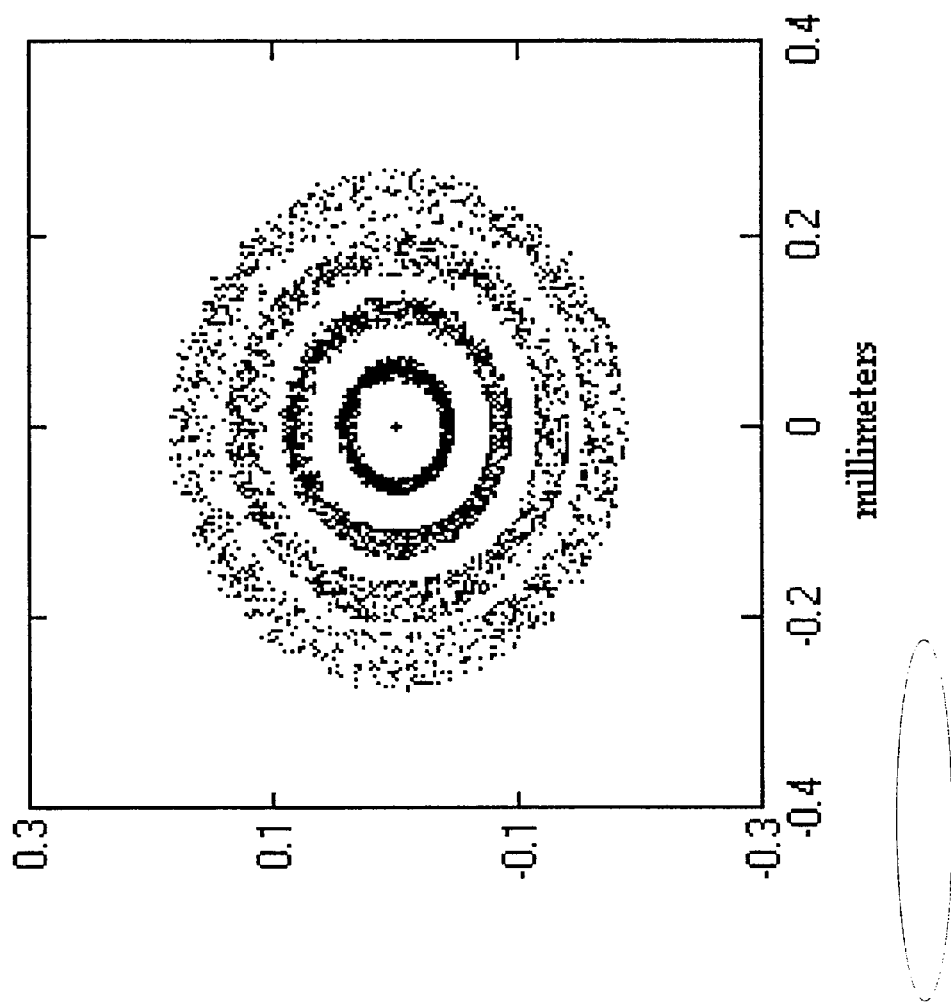
FIG. 9 shows ray tracing through an x-ray microscope. Resolutions better than $0.1\mu$ are achievable across a reasonable field of view.

The design class for x-ray microscopes using spherical optics and near-spherical correctors is extremely broad and versatile. For example, by using a series of four small spheres in sequence, starting a millimeter from a sample, one can create a coma-corrected image with resolution of less than one tenth of a micron, magnified to the level where the $10\mu$ pixels of a CCD can resolve the features. The entire microscope is less than one meter in length from the source to the detector. FIG. 8 diagrammatically shows the layout of an x-ray microscope comprising grazing incidence optics and compares it to a conventional light microscope. Radiation is generated in a source 74. The light microscope uses a condenser 73 to refocus light on the target 72. The x-ray source, being large, usually does not need a condenser. Radiation enters the microscope lens 71, which in the case of the x-ray optic is a four element coma-corrected set of spheres. The magnified image is then focused on the detector 70. In FIG. 9, ray tracing of concentric circles at $0.2\mu$ spacing shows the resolution produced by the grazing incidence x-ray microscope is near 0.1 $\mu$.

Figure 10:
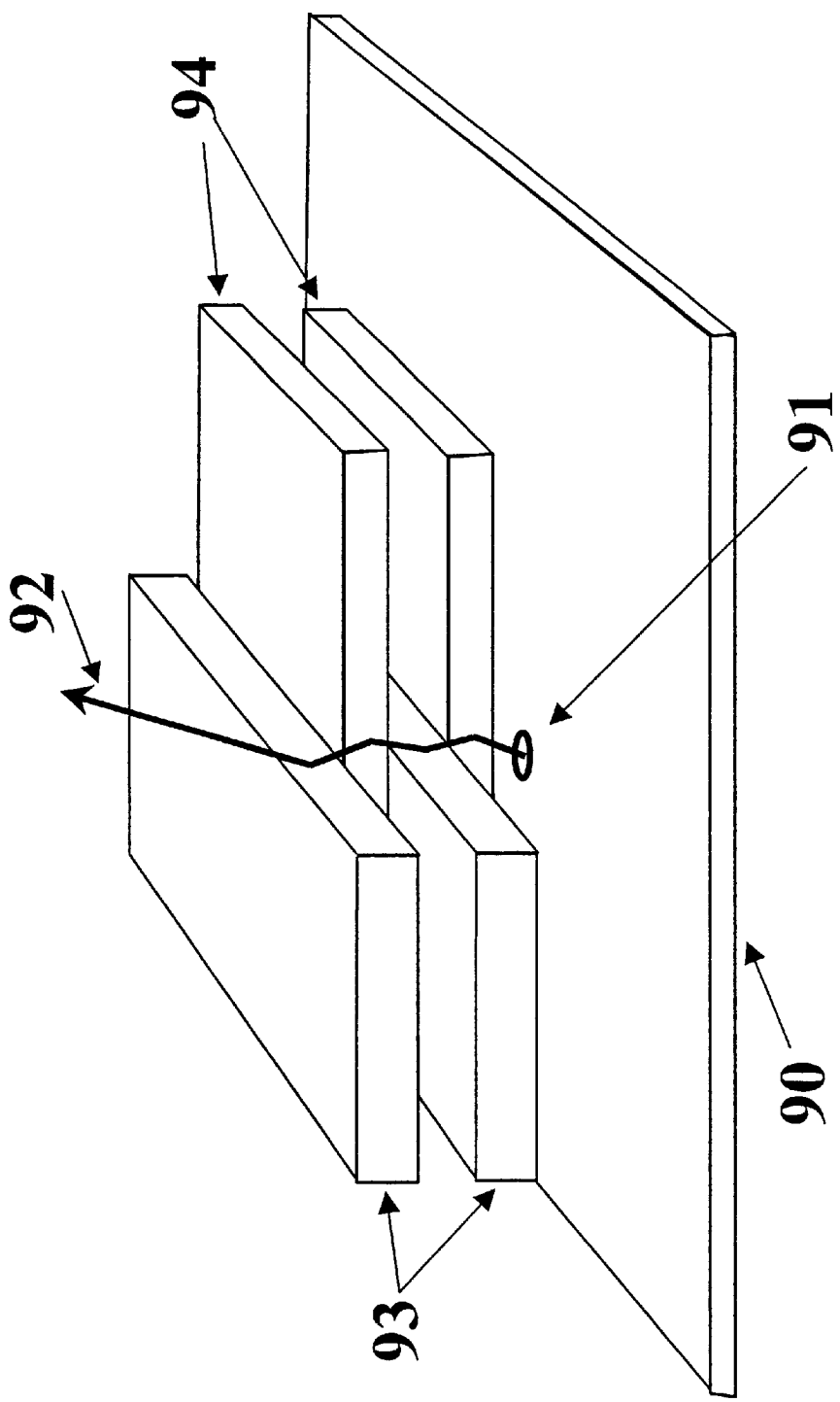
FIG. 10 shows how a four element spherical lens can be simply built by cutting slivers out of full sized polished blanks and stacking them.

FIG. 10 shows how small four-element spherical surface mirrors stacked to form a coma-corrected compound lens. X-rays 92 pass through a small hole 91 in a plate 90. Four spheres (93 and 94) have been sliced and stacked so that the x-ray reflects at a grazing angle off each sequentially. While the exemplary preferred embodiments of the present invention are described herein with particularity, those having ordinary skill in the art will recognize various changes, modifications, additions, and applications other than those specifically described herein, and may adapt the preferred embodiments and methods without departing from the spirit of the invention.

All documents cited herein are incorporated herein by reference.

I claim:

1. An apparatus for performing x-ray radio-surgery on a selected region of a patient, said apparatus comprising:
   an x-ray source generating orthovoltage x-ray radiation; and
   an optic focusing x-ray radiation from said x-ray source onto a selected region of a patient, so that the intensity of the focused x-ray radiation does not decrease by the square of the distance from the source and the intensity of focused x-ray radiation at the selected region is greater than the intensity of x-ray radiation entering the patient.

2. The apparatus of claim 1 wherein said optic comprises Wolter optics.

3. The apparatus of claim 1 wherein said optic comprises Kirkpatrick-Baez optics.

4. The apparatus of claim 1 wherein said optic comprises spherical reflectors.

5. The apparatus of claim 1 further comprising means for rotating said x-ray source and optic through a prescribed arc about the selected region of the patient, so that said focused x-ray radiation from said optic remains focused on the selected region of the patient.

6. The apparatus of claim 5 further comprising a detector located on the opposing side of the selected region of the patient from said x-ray source and rotating with said x-ray source to produce an x-ray image of the selected region of the patient.

7. A method for performing x-ray radio-surgery on a selected region of a patient comprising:
   generating orthovoltage x-ray radiation from an x-ray source;
   focusing said x-ray radiation on a selected region of a patient, so that the intensity of the focused x-ray radiation does not decrease by the square of the distance from the source; and rotating said focused x-ray radiation about the selected region of the patient, so that said focused x-ray radiation remains focused on the selected region of the patient and the intensity of x-ray radiation at the selected region is greater than the intensity of x-ray radiation at the patient's skin.

8. The method of claim 7 wherein x-ray radiation is focused by means of Wolter optics.

9. The method of claim 7 wherein x-ray radiation is focused by means of Kirkpatrick-Baez optics.

10. The method of claim 7 wherein x-ray radiation is focused by means of spherical reflectors.

11. The method of claim 7 further comprising the initial step of introducing a contrast element into the selected region of the patient.

* * * * *